United States Patent
Tatke et al.

(10) Patent No.: US 8,537,181 B2
(45) Date of Patent: Sep. 17, 2013

(54) MODES AND INTERFACES FOR OBSERVATION, AND MANIPULATION OF DIGITAL IMAGES ON COMPUTER SCREEN IN SUPPORT OF PATHOLOGIST'S WORKFLOW

(75) Inventors: Lokesh M. Tatke, Sunnyvale, CA (US); Christopher L. Gammage, Sunnyvale, CA (US); Robert J. Monroe, Sunnyvale, CA (US); Gregory C. Loney, Los Altos, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 781 days.

(21) Appl. No.: 12/720,579

(22) Filed: Mar. 9, 2010

(65) Prior Publication Data
US 2010/0225668 A1    Sep. 9, 2010

Related U.S. Application Data

(60) Provisional application No. 61/158,686, filed on Mar. 9, 2009.

(51) Int. Cl.
G09G 5/00    (2006.01)

(52) U.S. Cl.
USPC .......................... 345/672; 345/660

(58) Field of Classification Search
None
See application file for complete search history.

(56) References Cited

U.S. PATENT DOCUMENTS

| | | | |
|---|---|---|---|
| 4,635,293 A | | 1/1987 | Watanabe |
| 5,714,756 A | * | 2/1998 | Park et al. .......... 850/6 |
| 5,721,433 A | * | 2/1998 | Kosaka .......... 250/573 |
| 5,818,525 A | | 10/1998 | Elabd |
| 5,939,719 A | * | 8/1999 | Park et al. .......... 850/1 |
| 6,195,093 B1 | | 2/2001 | Nelson et al. |
| 6,396,941 B1 | * | 5/2002 | Bacus et al. .......... 382/128 |
| 6,785,427 B1 | | 8/2004 | Zhou et al. |
| 7,035,478 B2 | * | 4/2006 | Crandall et al. .......... 382/284 |
| 7,333,120 B2 | * | 2/2008 | Venolia .......... 345/661 |
| 2002/0018589 A1 | | 2/2002 | Beuker et al. |
| 2003/0048949 A1 | | 3/2003 | Bern et al. |
| 2005/0104902 A1 | | 5/2005 | Zhang et al. |
| 2005/0123211 A1 | | 6/2005 | Wong et al. |
| 2006/0028549 A1 | | 2/2006 | Grindstaff et al. |
| 2006/0098737 A1 | | 5/2006 | Sethuraman et al. |
| 2006/0204072 A1 | | 9/2006 | Wetzel et al. |
| 2006/0213994 A1 | | 9/2006 | Faiz et al. |
| 2007/0030529 A1 | | 2/2007 | Eichorn et al. |
| 2007/0069158 A1 | * | 3/2007 | Ohnishi .......... 250/492.22 |
| 2008/0240613 A1 | | 10/2008 | Dietz |
| 2009/0039260 A1 | * | 2/2009 | Ohnishi .......... 250/309 |
| 2011/0037779 A1 | * | 2/2011 | Liang .......... 345/661 |

FOREIGN PATENT DOCUMENTS

WO    WO-2008-118886 A1    10/2008

OTHER PUBLICATIONS

PCT/US08/58077 Written Opinion dated Aug. 21, 2008.
PCT/US08/58077 IPRP dated Aug. 21, 2008.

* cited by examiner

*Primary Examiner* — Ryan R Yang
(74) *Attorney, Agent, or Firm* — Ventana Medical Systems, Inc.

(57) ABSTRACT

Disclosed herein, in certain embodiments, is a method of manipulating a microscopy slide image. Disclosed herein, in certain embodiments, is a method of panning across the entire width and height of a microscopy slide image. Disclosed herein, in certain embodiments, is a method of changing the magnification of a microscopy slide image.

28 Claims, 1 Drawing Sheet

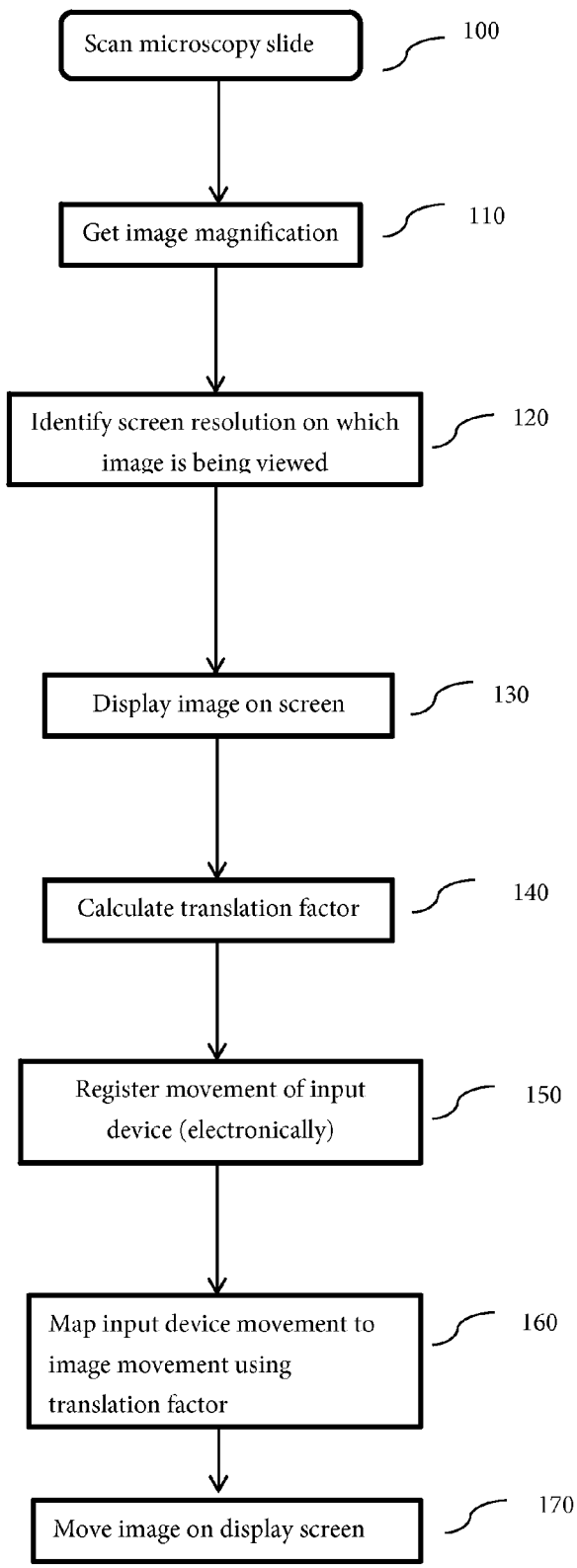

MODES AND INTERFACES FOR OBSERVATION, AND MANIPULATION OF DIGITAL IMAGES ON COMPUTER SCREEN IN SUPPORT OF PATHOLOGIST'S WORKFLOW

CROSS-REFERENCE

This application claims the benefit of U.S. Provisional Application No. 61/158,686, filed Mar. 9, 2009, which application is incorporated herein by reference.

BACKGROUND OF THE INVENTION

Microscopy allows one to identify both macroscopic and microscopic cellular structures displaying abnormal characteristics. In certain instances, these abnormalities are indicative of a particular disorder. In some instance, identification of these abnormalities facilitates the further diagnosis of a particular disorder. Microscopy is applicable to microbiology (e.g., gram staining, etc.), plant tissue culture, animal cell culture (e.g. phase contrast microscopy, etc.), molecular biology, immunology (e.g., ELISA, etc.), an d cell biology (e.g., immunofluorescence, chromosome analysis).

SUMMARY OF THE INVENTION

Disclosed herein in certain embodiments is a method of manipulating a microscopy slide image on a screen, comprising moving the slide image on the screen by translating a movement on an electronic input device in communication with the screen wherein movement on the electronic device produces a shift of the slide image on the screen by an amount that is equal to 0.7 to 1.3 of the shift on the electronic device multiplied by the image magnification.

Also disclosed in is a method wherein movement on the electronic device produces a shift of the slide image on the screen by an amount that is equal to 0.7 to 1.3 the shift on the electronic device multiplied by the image magnification and further multiplied by a sensitivity factor.

In one embodiment the sensitivity factor is from 1 to 20.

Disclosed herein, in certain embodiments, is a method of manipulating a microscopy slide image, comprising: scanning an microscopy slide image into a computer; identifying the magnification of the image; identifying the resolution of the screen on which the image is being viewed; determining the translation factor; displaying the image on a display screen; electronically registering the movement of an input device; applying the translation factor to the image being displayed on the display screen; and moving the image on the display screen. In some embodiments, the display screen is a high resolution screen. In some embodiments, the display screen is a standard resolution screen. In some embodiments, the input device is a keyboard; a mouse; a mini-mouse; a trackball; a scroll wheel; a touchpad; a graphics tablet; a touch-screen; an isotonic joysticks; a joystick; an analog stick; an isometric joystick; a pointing stick; a graphics tablet with a pen; a palm mouse; a footmouse; a puck; an eyeball-controlled mouse; a finger-mouse; a gyroscopic mouse; a light pen; a light gun; an eye tracking device; a steering wheel; a yoke; a jog dial; a spaceball; or a soap mouse. In some embodiments, the input device is a keyboard. In some embodiments, the input device is a mouse. In some embodiments, the input device is a scroll wheel. In some embodiments, the movement of the input device results in the image being moved on the display screen a proportionate distance. In some embodiments, the movement of the microscopy slide image is oriented in the same direction as the movement would be if viewed under the microscope. In some embodiments, movement of the input device along one vector triggers a corresponding movement in the opposite vector along the same axis in the display image. In some embodiments, movement of the input device along one vector triggers a corresponding movement in the same vector along the same axis in the display image. In some embodiments, the movement of the input device results in a change in the magnification of the image. In some embodiments, the movement of the input device allows a user to select a magnification of 1×2×, 4×, 10×, 20×, 40×, 60×, 80×, 100× or 120×; wherein the 80× magnification may be a digital zoom based on a 40× magnification and 120× magnification may be a digital zoom based on a 60× magnification. In some embodiments, the movement of the input device allows a user to select a magnification between 1× and 120×. In some embodiments, a user views a microscopy slide image at a higher magnification than the actual scan magnification. In some embodiments, a user increases the magnification of an image by use of digital zoom.

Disclosed herein, in certain embodiments, is a method of manipulating a microscopy slide image by use of a touch-screen, comprising: obtaining the display dimensions of the touch-screen; displaying the slide image on the touch-screen; displaying the image on a display screen associated with a desktop computer or a laptop; changing the default resolution of the image on the screen of the touch-screen; calculating the translation factor from the motion on the touch-screen to the high-resolution monitor; tracking movement within the display area; and applying the translation factor to the image being displayed on the high-resolution monitor screen.

Disclosed herein, in certain embodiments, is a system for manipulating a microscopy slide image, comprising: a means for scanning an microscopy slide image into a computer; a means for identifying the magnification of the image; a means for identifying the resolution of the screen on which the image is being viewed; a means for determining the translation factor; displaying the image on a display screen; a means for electronically registering the movement of an input device; a means for applying the translation factor to the image being displayed on the display screen; and a means for moving the image on the display screen. In some embodiments, the display screen is a high resolution screen. In some embodiments, the display screen is a standard resolution screen. In some embodiments, the input device is a keyboard; a mouse; a mini-mouse; a trackball; a scroll wheel; a touchpad; a graphics tablet; a touch-screen; an isotonic joysticks; a joystick; an analog stick; an isometric joystick; a pointing stick; a graphics tablet with a pen; a palm mouse; a footmouse; a puck; an eyeball-controlled mouse; a finger-mouse; a gyroscopic mouse; a light pen; a light gun; an eye tracking device; a steering wheel; a yoke; a jog dial; a spaceball; or a soap mouse. In some embodiments, the input device is a keyboard. In some embodiments, the input device is a mouse. In some embodiments, the input device is a scroll wheel. In some embodiments, the movement of the input device results in the image being moved on the display screen a proportionate distance. In some embodiments, the movement of the microscopy slide image is oriented in the same direction as the movement would be if viewed under the microscope. In some embodiments, movement of the input device along one vector triggers a corresponding movement in the opposite vector along the same axis in the display image. In some embodiments, movement of the input device along one vector triggers a corresponding movement in the same vector along the same axis in the display image. In some embodiments, the movement of the input device results in a change in the magnification of the image. In some embodiments, the movement of the input device allows a user to select a magnification of 1×, 2×, 4×, 10×, 20×, 40×, 60×, 80×, 100× or 120×. In some embodiments, the movement of the input device allows a user to select a magnification between 1× and 120×. In some embodiments, a user views a microscopy slide image at a higher magnification than the actual scan magnification. In some embodiments, a user increases the magnification of an image by use of digital zoom.

Disclosed in certain embodiments is a system for manipulating a microscopy slide image on a screen, comprising a screen for visualizing the slide image and an electronic input device in communication with the screen wherein movement on the electronic device produces a shift of the slide image on the screen by an amount that is equal to 0.7 to 1.3 of the shift on the electronic device multiplied by the image magnification.

Disclosed herein, in certain embodiments, is a system for manipulating a microscopy slide image by use of a touch-screen, comprising: a means for obtaining the display dimensions of the touch-screen; a means for displaying the slide image on the touch-screen; a means for displaying the image on a display screen associated with a desktop computer or a laptop; a means for changing the default resolution of the image on the screen of the touch-screen; a means for calculating the translation factor from the motion on the touch-screen to the high-resolution monitor; a means for tracking movement within the display area; and a means for applying the translation factor to the image being displayed on the high-resolution monitor screen.

BRIEF DESCRIPTION OF DRAWINGS

FIG. 1 illustrates an exemplary method of manipulating a microcopy slide in accordance with the present invention.

DETAILED DESCRIPTION OF THE INVENTION

Microscopy slides (e.g., those comprising tissue samples, and microbial samples) are being digitized (i.e., scanned into computers).

In certain instances, the scanning of these slides occurs at a very high magnification. In some embodiments, a slide is scanned at 20× magnification. In some embodiments, a slide is scanned at 0.46 microns/pixel. In some embodiments, a slide is scanned at 40× magnification. In some embodiments, a slide is scanned at 0.23 microns/pixel. In some embodiments, a scan of a slide comprises about 30,000× about 30,000 pixels. In some embodiments, a scan of a slide comprises about 100,000× about 120,000 pixels.

In certain instances, a display screen for a computer has a resolution of 1024×768 pixels. In certain instances, a display screen for a computer has a resolution of 1920×1280 pixels. In certain instances, an entire scanned image of a microscope slide cannot be displayed in a single screen at the scanned resolution. In certain instances, analysis of an entire microscope scanned image requires that a user pan across an image.

In certain instances, a user pans across a computer image by physically moving a "pointing device." In certain instances, the movements of an input device are reflected on a display screen. As used herein, "pointing device" and "input device" have the same meaning. As used herein, they mean an interface that allows a user to input spatial (i.e., continuous and multi-dimensional) data into a computer. Pointing devices include, but are not limited to, a keyboard, a mouse; a mini-mouse; a trackball; a touchpad; a graphics tablet; a touch-screen; an isotonic joysticks; a joystick; an analog stick; an isometric joystick; a pointing stick; a graphics tablet with a pen; a palm mouse; a footmouse; a puck; an eyeball-controlled mouse; a finger-mouse; a gyroscopic mouse; a light pen; a light gun; an eye tracking device; a steering wheel; a yoke; a jog dial; a spaceball; and a soap mouse.

In certain instances, the motion of a slide image across a computer screen occurs in pixels. In certain instances, an investment of a significant amount of time is required to pan from one end of a scanned microscopy slide image to the other end. In certain instances, panning from one end of a scanned microscopy slide image to the other end requires a significant amount of repetitive interaction with an input device. In certain instances, the motion input required from a user to move from one end of an image of a microscopy slide to the other end is more than would be required to move the actual slide.

Method

Disclosed herein, in certain embodiments, is a method of manipulating a microscopy slide image. In some embodiments, a microscopy slide image is viewed on a display monitor physically tethered to a computer (e.g., a desktop display screen or a laptop display screen). In some embodiments, a method of manipulating a microscopy slide image comprises: (a) scanning an microscopy slide image into a computer; (b) identifying the magnification of the image; (c) identifying the resolution of a display screen on which the image is being viewed; and (d) displaying the image on the display screen. In some embodiments, the scanning of the microscopy image into a computer is accomplished in any suitable manner. In some embodiments, the display screen is a standard resolution screen (i.e., has a resolution of about 1024× about 768 pixels). In preferable embodiments, the display screen is a high resolution screen (i.e., has a resolution of about 1920× about 1280 pixels).

A method disclosed herein utilizes any software program or application that allows a user to view a digital representation of a scanned microscopy slide.

Manipulation of Image Movement

Disclosed herein, in certain embodiments, is a method of panning across the entire width and height of a microscopy slide image. In some embodiments, the microscopy slide image is displayed on a display monitor physically tethered to a computer (e.g., a desktop display screen or a laptop display screen).

In some embodiments, a method of manipulating a microscopy slide image, as shown in FIG. 1, comprises palming across the entire width and height of a microscopy slide image. In some embodiments, panning across the entire width and height of a microscopy slide image comprises: in step 100, scanning an microscopy slide image into a computer; in step 110, identifying the magnification of the image; in step 120 identifying the resolution of the screen on which the image is being viewed; in step 130, displaying the image on the display screen; in step 140, calculating the factor by which the amount of real world motion is translated into an equivalent amount of motion of the microscopy slide image (the "translation factor"); in step 150, electronically registering the movement of an input device; in step 160, applying the translation factor to the image being displayed on the display screen; and in step 170, moving the image on the display screen.

Disclosed herein, in certain embodiments, is a system for manipulating a microscopy slide image, comprising: a means for scanning an microscopy slide image into a computer; a means for identifying the magnification of the image; a means for identifying the resolution of the screen on which the image is being viewed; a means for determining the translation factor; displaying the image on a display screen; a means for electronically registering the movement of an input device; a means for applying the translation factor to the image being displayed on the display screen; and a means for moving the image on the display screen.

The Translation Factor

In some embodiments, the amount of user input spatial data required to pan across a microscopy slide image is substantially the same as amount of motion required to move an actual slide. In some embodiments, the actual motion of the glass slide in millimeters is equivalent to the actual motion of the pointing device in millimeters.

In some embodiments, the amount of user input spatial data required to pan across a microscopy slide image is 1 times more than the amount of motion required to move an actual slide. In some embodiments, the amount of user input spatial data required to pan across a microscopy slide image is 1.5 times more than the amount of motion required to move an actual slide. In some embodiments, the amount of user input spatial data required to pan across a microscopy slide image is 2 times more than the amount of motion required to move an actual slide. In some embodiments, the amount of user input spatial data required to pan across a microscopy slide image is 2.5 times more than the amount of motion required to move an actual slide. In some embodiments, the amount of user input spatial data required to pan across a microscopy slide image is 3 times more than the amount of motion required to move an actual slide. In some embodiments, the amount of user input spatial data required to pan across a microscopy slide image is 4 times more than the amount of motion required to move an actual slide. In some embodiments, the amount of user input spatial data required to pan across a microscopy slide image is 5 times more than the amount of motion required to move an actual slide. In some embodiments, the amount of user input spatial data required to pan across a microscopy slide image is 10 times more than the amount of motion required to move an actual slide.

In some embodiments, the movement of an input device (during the pan process) is scaled according to the magnification at which the image is being viewed (i.e., scaled by the translation factor). By way of example only, if a slide has a tissue area of 15 mm×15 mm then a 20× equivalent scan of that slide would generate and image that would be 32,608×32608 pixels. The motion of the pointing device will be scaled such that if the pointing device is positioned at the left of the image and the user starts the pan motion, then the entire image width will be covered by moving the pointing device by 15 mm.

Input Devices

A method disclosed herein requires an input device to trigger the motion of the digital representation of a scanned microscopy slide on a display screen; however, a method disclosed herein, does not require a specific type of input device. Any commercially available input device (e.g., a keyboard; a mouse; a mini-mouse; a trackball; a touchpad; a graphics tablet; a touch-screen; an isotonic joysticks; a joystick; an analog stick; an isometric joystick; a pointing stick; a graphics tablet with a pen; a palm mouse; a footmouse; a puck; an eyeball-controlled mouse; a finger-mouse; a gyroscopic mouse; a light pen; a light gun; an eye tracking device; a steering wheel; a yoke; a jog dial; a spaceball; and a soap mouse) is contemplated for use with a method disclosed herein.

In some embodiments, physical movement of an input device triggers the motion of the digital representation of a scanned microscopy slide on a display screen. In some embodiments, the input device is a keyboard; a mouse; a mini-mouse; a trackball; an isotonic joysticks; a joystick; an analog stick; an isometric joystick; a pointing stick; a palm mouse; a footmouse; a puck; an eyeball-controlled mouse; a finger-mouse; a gyroscopic mouse; a light pen; a light gun; an eye tracking device; a steering wheel; a yoke; a jog dial; a spaceball; or a soap mouse.

In some embodiments, the input device requires a flat surface (i.e., it moves in two dimensional space). In some embodiments, the input device is a mouse. In some embodiments, the mouse is physically connected to the display monitor (or to computer connected to the display monitor).

In some embodiments all the devices are connected to the computer/laptop including a display screen which may be connected to the computer/laptop whereby commands are sent from the device to the computer and the display reacts accordingly.

In some embodiments, the mouse is wirelessly (e.g., by BLUETOOTH technology) connected to the display monitor (or to computer connected to the display monitor).

In some embodiments, the input device is a scroll wheel. As used herein, a "scroll wheel" includes both mechanical scroll wheels and touch sensitive scroll wheels. In some embodiments, the scroll wheel scrolls horizontally and/or vertically.

In some embodiments, the input device moves in two dimensions (i.e., along the x-axis and the y-axis). In some embodiments, the input device moves in three dimensions (i.e., along the x-axis, the y-axis, and the z-axis). For example, the up and down may result in a motion along the Y axis and the left and right may result in a motion along the X axis Microscopy Mimicking Motions In some embodiments, the movement of the microscopy slide image is oriented in the same direction as the movement would be if viewed under the microscope. In some embodiments, moving an input device up will move the microscopy slide image down. In some embodiments, moving an input device down will move the microscopy slide image up. In some embodiments, moving an input device to the right will move the microscopy slide image to the left. In some embodiments, moving an input device to the left will move the microscopy slide image to the right. This concept allows a user of microscope to have a similar experience while viewing a digitally scanned image on a computer screen.

In some embodiments, the input device is a computer keyboard. In some embodiments, depression of an up-arrow key (i.e., a key displaying the "↑" character) results in movement in a negative vector along the x-axis. In some embodiments, depression of a down-arrow key (i.e., a key displaying the "↓" character) results in movement in a positive vector along the x-axis. In some embodiments, depression of an left-arrow key (i.e., a key displaying the "←→" character) results in movement in a positive vector along the y-axis. In some embodiments, depression of a right-arrow key (i.e., a key displaying the "→" character) results in movement in a negative vector along the y-axis. The foregoing should not be construed as limiting the key choices available for use with the present method.

In some embodiments, movement of the input device along one vector triggers a corresponding movement in the opposite vector along the same axis in the display image. In some embodiments, movement of the input device in a positive vector along the z-axis results in the image moving in a negative vector along the z-axis. In some embodiments, movement of the input device in a negative vector along the z-axis results in the image moving in a positive vector along the z-axis. In some embodiments, movement of the input device in a positive vector along the x-axis results in the image moving in a negative vector along the x-axis. In some embodiments, movement of the input device in a negative vector along the x-axis results in the image moving in a positive vector along the x-axis. In some embodiments, movement of the input device in a positive vector along the y-axis results in the image moving in a negative vector along the y-axis. In some embodiments, movement of the input device in a negative vector along the y-axis results in the image moving in a positive vector along the y-axis.

In some embodiments, the input device requires a flat surface (i.e., it moves in two dimensional space). In some embodiments, the input device is a mouse. In some embodiments, movement of the mouse in a positive vector along the x-axis results in the image moving in a negative vector along the x-axis. In some embodiments, movement of the mouse in a negative vector along the x-axis results in the image moving in a positive vector along the x-axis. In some embodiments, movement of the mouse in a positive vector along the y-axis results in the image moving in a negative vector along the y-axis. In some embodiments, movement of the mouse in a negative vector along the y-axis results in the image moving in a positive vector along the y-axis.

In some embodiments, the input device is a scroll wheel. In some embodiments, movement of the scroll wheel in a positive vector along the x-axis results in the image moving in a negative vector along the x-axis. In some embodiments, movement of the scroll wheel in a negative vector along the x-axis results in the image moving in a positive vector along the x-axis. In some embodiments, movement of the scroll wheel in a positive vector along the y-axis results in the image moving in a negative vector along the y-axis. In some embodiments, movement of the scroll wheel in a negative vector along the y-axis results in the image moving in a positive vector along the y-axis.

Natural Motion

In some embodiments, the movement of the microscopy slide image is oriented in the opposite direction as the movement would be if viewed under the microscope. In some embodiments, moving an input device up will move the microscopy slide image up. In some embodiments, moving an input device down will move the microscopy slide image down. In some embodiments, moving an input device to the right will move the microscopy slide image to the right. In some embodiments, moving an input device to the left will move the microscopy slide image to the left.

In some embodiments, the input device is a computer keyboard. In some embodiments, depression of an up-arrow key (i.e., a key displaying the "↑" character) results in movement in a positive vector along the x-axis. In some embodiments, depression of a down-arrow key (i.e., a key displaying the "↓" character) results in movement in a negative vector along the x-axis. In some embodiments, depression of an left-arrow key (i.e., a key displaying the "←→" character) results in movement in a negative vector along the y-axis. In some embodiments, depression of a right-arrow key (i.e., a key displaying the "→" character) results in movement in a positive vector along the y-axis. The foregoing should not be construed as limiting the key choices available for use with the present method.

In some embodiments, movement of the input device along one vector triggers a corresponding movement in the same vector along the same axis in the display image. In some embodiments, movement of the input device in a positive vector along the z-axis results in the image moving in a positive vector along the z-axis. In some embodiments, movement of the input device in a negative vector along the z-axis results in the image moving in a negative vector along the z-axis. In some embodiments, movement of the input device in a positive vector along the x-axis results in the image moving in a positive vector along the x-axis. In some embodiments, movement of the input device in a negative vector along the x-axis results in the image moving in a negative vector along the x-axis. In some embodiments, movement of the input device in a positive vector along the y-axis results in the image moving in a positive vector along the y-axis. In some embodiments, movement of the input device in a negative vector along the y-axis results in the image moving in a negative vector along the y-axis.

In some embodiments, the input device requires a flat surface (i.e., it moves in two dimensional space). In some embodiments, the input device is a mouse. In some embodiments, movement of the mouse in a positive vector along the x-axis results in the image moving in a positive vector along the x-axis. In some embodiments, movement of the mouse in a negative vector along the x-axis results in the image moving in a negative vector along the x-axis. In some embodiments, movement of the mouse in a positive vector along the y-axis results in the image moving in a positive vector along the y-axis. In some embodiments, movement of the mouse in a negative vector along the y-axis results in the image moving in a negative vector along the y-axis.

In some embodiments, the input device is a scroll wheel. In some embodiments, movement of the scroll wheel in a positive vector along the x-axis results in the image moving in a positive vector along the x-axis. In some embodiments, movement of the scroll wheel in a negative vector along the x-axis results in the image moving in a negative vector along the x-axis. In some embodiments, movement of the scroll wheel in a positive vector along the y-axis results in the image moving in a positive vector along the y-axis. In some embodiments, movement of the scroll wheel in a negative vector along the y-axis results in the image moving in a negative vector along the y-axis.

Manipulation via Use of Touch-Screens

Disclosed herein, in certain embodiments, is a system for manipulating a microscopy slide image by use of a touch-screen. As used herein, touch-screen refers to any display monitor that detects the presence and movement of a touch within the display area. Touch-screens include, but are not limited to, resistive panel touch-screens, surface acoustic wave panel touch-screens, capacitive panel touch-screens, optical touch-screens, strain gauge touch-screens, optical imaging touch-screens, dispersive signal technology touch-screens, and acoustic pulse recognition touch-screens. By way of non-limiting example, a touch screen includes a smart phone, a graphics pad, and a graphics tablet/screen hybrid. As used herein, "touch" refers to contact between the display of the device and a foreign object (e.g., a finger or a stylus).

In some embodiments, the touch-screen connects to a server associated with a computer with a high resolution monitor. In some embodiments, the connection is a wireless connection. In some embodiments, a method of manipulating a microscopy slide image by use of a touch-screen comprises: (a) obtaining the display dimensions of the touch-screen; (b) displaying the slide image on the touch-screen; (c) displaying the image on a display screen associated (e.g., physically connected or wirelessly connected) with a desktop computer or a laptop; (d) changing the default resolution of the image on the screen of the touch-screen; (e) calculating the translation factor from the motion on the touch-screen to the high-resolution monitor; (f) tracking movement within the display area; and (g) applying the translation factor to the image being displayed on the high-resolution monitor screen.

Disclosed herein, in certain embodiments, is a system for manipulating a microscopy slide image by use of a touch-screen, comprising: a means for obtaining the display dimensions of the touch-screen; a means for displaying the slide image on the touch-screen; a means for displaying the image on a display screen associated with a desktop computer or a laptop; a means for changing the default resolution of the image on the screen of the touch-screen; a means for calculating the translation factor from the motion on the touch-screen to the high-resolution monitor; a means for tracking movement within the display area; and a means for applying the translation factor to the image being displayed on the high-resolution monitor screen.

Manipulation of Magnification

Disclosed herein, in certain embodiments, is a method of changing the magnification of a microscopy slide image. In some embodiments, an input device enables a user to change the magnification of a microscopy slide image. In some embodiments, an input device enables a user select a magnification of 1×, 2×, 4×, 10×, 20×, 40×, 60×, 80×, 100× or 120×. In some embodiments, an input device enables a user select any magnification between 1× and 120×. In some embodiments, a user views a microscopy slide image at a higher magnification than the actual scan magnification. In some embodiments, a user increases the magnification of an image by use of digital zoom.

In some embodiments, movement of an input device results in a change in the magnification of an image. In some embodiments, moving the input device in a positive vector along the x-axis increases the magnification of the image. In some embodiments, moving the input device in a negative vector along the x-axis decreases the magnification of the image. In some embodiments, the input device is a mouse (e.g., a wireless mouse or a physically attached mouse).

In some embodiments, an input device comprises a scroll wheel. In some embodiments, manipulation of a scroll wheel results in a change in the magnification of an image. In some embodiments, moving the scroll wheel in a positive vector along the x-axis (i.e., up) increases the magnification. In some embodiments, moving the scroll wheel in a negative vector along the x-axis (i.e., down) decreases the magnification.

In some embodiments, a scroll wheel manipulates magnification and the image position on the screen. In some embodiments, the default function of the scroll wheel is manipulation of the image position on the screen. In some embodiments, the secondary function of the scroll wheel is manipulation of magnification. In some embodiments, a user must actively select the secondary function (i.e., manipulation of magnification). In some embodiments, a user selects the secondary option by depressing a key or a combination of keys, for example and without limitation a "Ctrl" key may be depressed.

In some embodiments, the input device is a computer keyboard. In some embodiments, depression of an up-arrow key (i.e., a key displaying the "↑" character) results in an increase in magnification. In some embodiments, depression of a down-arrow key (i.e., a key displaying the "↓" character) results in a decrease in magnification. The foregoing should not be construed as limiting the key choices available for use with the present method. Any key can be designated as the key to depress to increase (or decrease magnification). For example, the "u" key can be designation as the key the depression of which will increase magnification, while depressing the "d" key will decrease magnification.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of manipulating a microscopy slide image on a screen, comprising moving the slide image on the screen by translating a movement on an electronic input device in communication with the screen wherein movement on the electronic device produces a shift of the slide image on the screen by an amount that is equal to 0.7 to 1.3 of the shift on the electronic device multiplied by the image magnification.

2. The method of claim 1, wherein movement on the electronic device produces a shift of the slide image on the screen by an amount that is equal to 0.7 to 1.3 the shift on the electronic device multiplied by the image magnification and further multiplied by a sensitivity factor.

3. The method of claim 2, wherein the sensitivity factor is from 1 to 20.

4. A method of manipulating a microscopy slide image on a screen, comprising moving the slide image on the screen by translating a movement on an electronic input device in communication with the screen wherein movement on the electronic device produces a shift of the slide image on the screen equivalent to a shift obtained when a pathology slide is moved under an optical microscope.

5. The method of claim 4, wherein an amount of user input spatial data required to pan across the slide image on the screen is 1.5 times more than the amount of motion required for moving the pathology slide under the optical microscope.

6. The method of claim 4, wherein an amount of user input spatial data required to pan across the slide image on the screen is essentially the same as an amount of motion required for moving the pathology slide under the optical microscope.

7. The method of claim 4, wherein portions of the image traveled while the image is being moved on the screen are visible to the operator while the image is being shifted.

8. The method of claim 4, wherein the input device is a touchpad;
a track pad, a graphics tablet; or a touch-screen.

9. The method of claim 4, wherein the input device is a keyboard; a mouse; a mini-mouse; a trackball; a scroll wheel; a touchpad; a graphics tablet;
a touch-screen; an isotonic joysticks; a joystick; an analog stick; an isometric joystick; a pointing stick; a graphics tablet with a pen; a palm mouse; a footmouse; a puck; an eyeball-controlled mouse; a finger-mouse; a gyroscopic mouse; a light pen; a light gun; an eye tracking device; a steering wheel; a yoke; a jog dial; a spaceball; or a soap mouse.

10. The method of claim 4, wherein the movement of the input device results in the image being moved on the display screen a distance proportionate to the magnification of the image.

11. The method of claim 4, wherein the movement of the microscopy slide image is oriented in the same direction as the movement would be if viewed under the microscope.

12. The method of claim 4, wherein the movement of the input device results in a change in the magnification of the image.

13. The method of claim 4, wherein the movement of the input device allows a user to select a magnification of 1×, 2×, 4×, 10×, 20×, 40×, 60×, 80×, 100× or 120×.

14. The method of claim 4, wherein the movement of the input device allows a user to select a magnification between 1× and 120×.

15. The method of claim 4, wherein a user views a microscopy slide image at a higher magnification than the actual scan magnification.

16. The method of claim 4, wherein a user increases the magnification of an image by use of digital zoom.

17. A method of manipulating a microscopy slide image on a screen, comprising moving the slide image on the screen by translating a movement on an electronic input device in communication with the screen wherein movement on the electronic device produces a shift of the slide image on the screen equivalent to a shift obtained when a pathology slide is moved under an optical microscope, wherein movement of the input device along one vector triggers a corresponding movement in the opposite vector along the same axis in the display image.

18. A method of manipulating a microscopy slide image on a screen, comprising moving the slide image on the screen by translating a movement on an electronic input device in communication with the screen wherein movement on the electronic device produces a shift of the slide image on the screen equivalent to a shift obtained when a pathology slide is moved under an optical microscope, wherein movement of the input device along one vector triggers a corresponding movement in the same vector along the same axis in the display image.

19. A method of manipulating a microscopy slide image, comprising:
    (a) scanning the microscopy slide image into a computer;
    (b) identifying a magnification of the image;
    (c) identifying a resolution of a screen on which the image is being viewed;
    (d) determining a translation factor;
    (e) displaying the image on a display screen;
    (f) electronically registering a movement of an input device;
    (g) applying the translation factor to the image being displayed on the display screen; and
    (h) moving the image on the display screen.

20. A method of manipulating a microscopy slide image by use of a touch-screen, comprising:
    (a) obtaining display dimensions of the touch-screen;
    (b) displaying the slide image on the touch-screen;
    (c) displaying the image on a display screen associated with a desktop computer or a laptop;
    (d) changing a default resolution of the image on the touch-screen;
    (e) calculating a translation factor from motion on the touch-screen to the display screen associated with the desktop computer or the laptop;
    (f) tracking movement within a display area of the touch-screen; and
    (g) applying the translation factor to the image being displayed on the display screen associated with the desktop computer or the laptop.

21. A system for manipulating a microscopy slide image on a screen, comprising a screen for visualizing the slide image and an electronic input device in communication with the screen wherein movement on the electronic device produces a shift of the slide image on the screen by an amount that is equal to 0.7 to 1.3 of the shift on the electronic device multiplied by the image magnification.

22. The system of claim 21, wherein the input device is a touchpad; a track pad, a graphics tablet; or a touch-screen.

23. The system of claim 21 further comprising a sensitivity multiplier wherein movement on the electronic device produces a shift of the slide image on the screen by an amount that is equal to 0.7 to 1.3 the shift on the electronic device multiplied by the image magnification and further multiplied by a sensitivity factor.

24. A system for manipulating a microscopy slide image, comprising:
    (a) a means for scanning the microscopy slide image into a computer;
    (b) a means for identifying a magnification of the image;
    (c) a means for identifying a resolution of a screen on which the image is being viewed;
    (d) a means for determining a translation factor;
    (e) a means for displaying the image on a display screen;
    (f) a means for electronically registering a movement of an input device;
    (g) a means for applying the translation factor to the image being displayed on the display screen; and
    (h) a means for moving the image on the display screen.

25. The system of claim 24, wherein the input device is a keyboard; a mouse; a mini-mouse; a trackball; a scroll wheel; a touchpad; a track pad; a graphics tablet; a touch-screen; an isotonic joysticks; a joystick; an analog stick; an isometric joystick; a pointing stick; a graphics tablet with a pen; a palm mouse; a footmouse;
    a puck; an eyeball-controlled mouse; a finger-mouse; a gyroscopic mouse; a light pen; a light gun; an eye tracking device; a steering wheel; a yoke; a jog dial; a spaceball; or a soap mouse.

26. The system of claim 24, wherein a user views the microscopy slide image at a higher magnification than the actual scan magnification.

27. The system of claim 24, wherein a user increases the magnification of the image by use of digital zoom.

28. A system for manipulating a microscopy slide image by use of a touch-screen, comprising:
    (a) a means for obtaining display dimensions of the touch-screen;
    (b) a means for displaying the slide image on the touch-screen;
    (c) a means for displaying the image on a display screen associated with a desktop computer or a laptop;
    (d) a means for changing a default resolution of the image on the touch-screen;
    (e) a means for calculating a translation factor from motion on the touch-screen to the display screen associated with the desktop computer or the laptop;
    (f) a means for tracking movement within a display area of the touch-screen; and
    (g) a means for applying the translation factor to the image being displayed on the display screen associated with the desktop computer or the laptop.

* * * * *